(12) United States Patent
Ali et al.

(10) Patent No.: US 8,325,342 B2
(45) Date of Patent: Dec. 4, 2012

(54) DETECTION METHOD

(75) Inventors: Zulfiqur Ali, Stokesley (GB); Lalitesh Nitin Seetohul, Middlesbrough (GB); Vincent David Auger, Hartlepool (GB); Meezanul Islam, Middlesbrough (GB); Simon Michael Scott, Stockton-on-Tees (GB)

(73) Assignee: Teesside University, Middlesbrough (GB)

( * ) Notice: Subject to any disclaimer, the term of this patent is extended or adjusted under 35 U.S.C. 154(b) by 446 days.

(21) Appl. No.: 12/517,117

(22) PCT Filed: Dec. 3, 2007

(86) PCT No.: PCT/GB2007/050734
§ 371 (c)(1),
(2), (4) Date: Jan. 22, 2010

(87) PCT Pub. No.: WO2008/065455
PCT Pub. Date: Jun. 5, 2008

(65) Prior Publication Data
US 2010/0141951 A1 Jun. 10, 2010

(30) Foreign Application Priority Data
Dec. 2, 2006 (GB) .................................. 0624148.3

(51) Int. Cl.
*G01N 21/00* (2006.01)
(52) U.S. Cl. ........................................ 356/436; 356/432
(58) Field of Classification Search ........... 356/436–440
See application file for complete search history.

(56) References Cited

U.S. PATENT DOCUMENTS

| | | | |
|---|---|---|---|
| 5,572,328 A * | 11/1996 | Fouckhardt et al. | ........... 356/440 |
| 6,100,541 A | 8/2000 | Nagle et al. | |
| 6,316,781 B1 | 11/2001 | Nagle et al. | |
| 2004/0207852 A1 | 10/2004 | Bechtel et al. | |
| 2005/0094158 A1 | 5/2005 | Paldus et al. | |
| 2005/0158868 A1 | 7/2005 | Trebbia et al. | |
| 2006/0072117 A1 * | 4/2006 | Ruth et al. | ..................... 356/453 |

(Continued)

FOREIGN PATENT DOCUMENTS
WO   99/44217 A   9/1999

OTHER PUBLICATIONS

Vallance, C., et al., "Broadband cavity-enhanced absorption spectroscopy for real time, in situ spectral analysis of microfluidic droplets," Lap on a Chip—Miniaturisation for Chemistry and Biology, vol. 11, Issue 23, Dec. 7, 2011, pp. 3953-3955.

(Continued)

*Primary Examiner* — Michael P Stafira
(74) *Attorney, Agent, or Firm* — Paul A. Jenny; Michael Best & Friedrich LLP

(57) ABSTRACT

The invention relates to an apparatus and method for the detection of the spectral absorption properties of a fluid in a microenvironment, the apparatus comprising a radiation source, a microfluidic device and detection means, wherein the apparatus additionally comprises means for increasing the path length of the radiation through the fluid. Preferably, the means for increasing the path length of the radiation through the fluid comprises two highly reflective mirrors which cause the base path length through the fluid to be increased by many orders of magnitude, and the method comprises Cavity Enhanced Absorption Spectroscopy. The method is especially useful for the handling of small volumes of fluids for chemical and biological processing.

16 Claims, 6 Drawing Sheets

Microfluidic device with CEAS detection

U.S. PATENT DOCUMENTS

2010/0011842 A1* 1/2010 Hoyle et al. .................. 73/61.41

OTHER PUBLICATIONS

Fiedler, S., et al., "Incoherent broad-band cavity-enhanced absorption spectroscopy of liquids," Review of Scientific Instruments, American Institute of Physics, US, vol. 76, No. 2, Jan. 10, 2005, pp. 23107-1-23107-7.

Islam, M., et al., "Liquid-phase broadband cavity-enhanced absorption spectroscopy measurements in a 2 mm cuvette," Applied Spectroscopy Society for Applied Spectroscopy USA, vol. 61, No. 6, Jun. 2007, pp. 649-658. (Abstract Only).

International Search Report from International Patent Application Publication No. WO2008/065455, dated Mar. 28, 2008.

* cited by examiner

Figure 1 Microfluidic device with CEAS detection

Figure 5 Micro-well plate with CEAS detection

DETECTION METHOD

CROSS REFERENCE TO RELATED APPLICATIONS

This is the national stage of International Application No. PCT/GB2007/050734, filed on Dec. 3, 2007, which claims the benefit of Great Britain Application No. 0624148.3, filed on Dec. 2, 2006, the contents of all of which are incorporated herein by reference.

FIELD OF THE INVENTION

The present invention is concerned with an apparatus and method for the determination of the absorption features of small volumes of fluids contained in microenvironments. More specifically, the invention relates to apparatus and methods for Cavity Enhanced Absorption Spectroscopy (CEAS) detection in microfluidic devices.

BACKGROUND OF THE INVENTION

A number of sectors of technology require greater exploration of both chemical and biological space and diversity. In the pharmaceutical sector, for example, the search for new drug candidate compounds is leading to compounds being made and screened at an ever increasing rate. The resulting increase in demand for chemical and biological information is driving innovations in the handling and detection of small volumes of liquids in microfluidic devices.

Microfluidics is a technology that allows the storage, dosing, movement and mixing of very small volumes of fluids and can be applied at the system, module and component level. The technology employs microfluidic components which may be either passive or active. Typically, passive components comprise miniaturised plates that may be functionalised, whilst active components are capable of performing either a unique function, such as sample preparation, or integrated functions, which could incorporate the combined operations of sample preparation, separation and detection.

Both active and passive components may comprise one or more channels which typically have dimensions in the range of micrometres to sub-millimetre, thereby yielding minimum handled volumes in the pL range. The fluidic architecture is formed in the substrate using a variety of microfabrication processes including etching, injection moulding, embossing, laser ablation and stamping. Fluid samples are typically contained and transported within these channels. Common fluids used in microfluidic devices includes whole blood samples and bacterial suspensions. Other features that can be formed in the substrate to contain the sample include well structures. Such microfluidic devices will be familiar to those of ordinary skill in the art.

Miniaturised plates employ a variety of substrates including glass or polymer and may be either planar or may comprise micro-well plates. Planar substrates that are functionalised with bioactive components are commonly known as biochips, and are used for monitoring ligand receptor binding. Micro-well plates, on the other hand, comprise an array of individual wells in a two-dimensional format. Increasing the density of micro-well plates provides some advantages in evaporation losses of the liquid, but also leads to increasing complexity in operations such as dispensing and detection. The dispensing of reagents into micro-well plates is generally performed using robotic systems.

Active microfluidic components which are required to perform a variety of integrated functions, such as sample preparation, separation and detection, require highly sophisticated manipulation of very small volumes of liquids. Sample separation may be performed by any of a variety of well known techniques including, for example, gel electrophoresis and chromatography. These active devices would be familiar to those of ordinary skill in the art, and are alternatively referred to as Lab-on-a-chip or μTAS. Such devices have a wide range of applications, including chemical and biological analysis, and high throughput screening, in addition to microreactor applications.

Many techniques of detection have been implemented in microfluidic devices, including spectroscopic and electrochemical detection. Specifically, absorbance methods can be applied by measuring across either the channel length or the channel width of a microfluidic device but, in view of the short path length in microfluidic devices, such techniques have the disadvantage of relatively low sensitivity in comparison to macroscopic devices.

Optical cavity methods are becoming more widely used as sensitive methods of absorbance measurements. These methods rely on light being confined between two highly reflective mirrors, thereby resulting in the base path length being increased by many orders of magnitude in the gas phase. The first implementation of this technique was Cavity Ring Down Spectroscopy (CRDS), which was proposed by O'Keefe and Deacon[1] in 1988. Typically, light from a pulsed laser or a continuous wave (CW) laser with a suitable interruption method is introduced into the cavity through the back of one of the mirrors. The 1/e decay time, known as the ring down time, of a pulse of laser light confined between the mirrors is then measured in the presence and absence of the sample and related to the absorption coefficient at a particular wavelength of the sample in the optical cavity. The wavelength can be scanned in most cases to record an absorption spectrum. However, the detection of the light exiting the cavity requires fast response detectors and associated equipment capable of measuring on the nanosecond timescale and this consideration, along with the expense of pulsed laser sources, makes most implementations of CRDS prohibitively expensive and inconvenient.

Subsequently, Englen et al[2] and O'Keefe[3] disclosed simpler variations of CRDS which they respectively named Cavity Enhanced Absorption Spectroscopy (CEAS) and Integrated Cavity Output Spectroscopy (ICOS) although, in essence, these techniques are equivalent. In the case of CEAS, a continuous wave light source is used which replenishes the light lost due to reflection inefficiencies and absorption by the sample. Englen et al have shown that light within the cavity reaches steady state within a few ring down times, and its intensity is proportional to the ring down time. Consequently, the sample absorbance can be determined by steady state intensity measurement in the presence and absence of the sample in the cavity and this means that slower response detectors can be used, thereby reducing the cost of the detection element of the experimental scheme. Unfortunately, however, a further consequence is that the absorption cross section now cannot be measured directly and, instead, a comparison with a reference compound in the cavity is firstly required.

Recently, simpler and cheaper light sources have also been proposed for such applications[4,5]. These include broadband light sources such as arc lamps or high intensity LEDs, both coupled with multiplex detection, thereby in principle allowing the measurement of the entire absorption spectrum in one action, rather than requiring scanning across the spectrum.

There is an associated disadvantage, however, which is typically manifested as a lower wavelength resolution for the absorption spectrum.

The CRDS and CEAS techniques have principally been used for the detection of gases which have narrow absorption features. More recently, however, these techniques have been used for the analysis of liquids in which most absorption features are relatively broad (several nanometers linewidth). Thus, Zare[6-8] has demonstrated the analysis of liquid samples using CRDS with an inexpensive diode laser source, whilst Ariese[9] has described CRDS in the liquid phase for Liquid Chromatography (LC) analysis using a cell made from a silicone rubber spacer clamped leak tight between two high reflectivity mirrors. The mirrors are in direct contact with the liquid flow.

Several prior art documents are available which disclose different multipass techniques, designed to enhance the path length of measurement. Thus, US-A-2005/0162652 teaches doubling the pathlength through microlitre sized liquid samples using LEDs together with a novel implementation of corner cube beamsplitters. However, the maximum enhancement over a conventional absorption measurement is a factor of two.

GB-A-2284904 is concerned with the use of a liquid core fibre optic as a waveguide to achieve long pathlengths in a liquid analyte by choosing a material for the construction of the waveguide which has a lower refractive index than the liquid core. Thus, light from a suitable light source passes along the waveguide through total internal reflection, such that the path length can, in principle, be doubled by using a mirror at one end of the fibre optic to reflect the light back.

U.S. Pat. No. B6,224,830 relates to the improvement of the sensitivity of absorption measurements in microfluidic devices by increasing the pathlength across a microchannel through depositing mirrors on opposite sides of the channel and using the channel as a waveguide to allow multiple reflections from the input and output end of the radiation source. Thus, the light source enters the waveguide and is reflected off the mirrors several times along the length of the fluidic channel as it progresses from the entrance to the exit port.

US-A-2005/0046851 discloses the doubling of the pathlength through a miniature gas cell using folded optics, the process involving depositing mirrors onto the surface of the gas cell. In this approach, the light source enters the gas cell and is reflected off the deposited mirror and onto the detector. Thus, the enhancement achieved using this approach is simply a doubling of the pathlength. Furthermore, the disclosed method is only relevant for measurements relating to gaseous systems.

U.S. Pat. No. B6,839,140 describes the application of cavity enhanced absorption spectroscopy (CEAS) to liquids. Thus, external mirrors of 2-4 mm diameter with typical mirror separations of 0.1-2 mm are assembled into a flow cell giving a minimum interrogated sample volume of 0.5 µL. Clearly, it would be desirable to provide systems with mirror separations of much smaller magnitude.

However, each of these approaches only allows the fluid to pass through the optical cavity, and there is no potential for the fluid to interact with a functionalised surface, or for the performance of complex micro and nanoscale volume fluidic operations, such as the mixing, direction and separation of reagent and sample streams in an integrated approach. Therefore, the existing techniques would be difficult to miniaturise for application to very small scale situations and also would not readily facilitate the creation of large numbers of devices (potentially thousands to millions).

Thus, the present invention seeks to provide a method and apparatus which overcomes the disadvantages associated with the prior art and allows for the measurement of parameters and detection of properties of fluids on a small scale contained in such as microfluidic devices.

Specifically, the present invention provides a system which is based on using an optical cavity to gain an enhancement of, in principle, greater than one hundredfold over conventional absorption spectroscopy. Furthermore, whilst the invention deals with the measurement of absorption parameters in small volumes of liquid, the mechanism for enhancement of sensitivity is based on CEAS and not total internal reflection, unlike many of the methods of the prior art.

Although the presently disclosed system requires the deposition of mirrors on a microfluidic device, the mechanism for increasing the sensitivity of the absorption measurement is entirely different to that which is employed in, for example, the prior art method of U.S. Pat. No. B6,224,830. Thus, in the present CEAS approach, the light source is transmitted through the entrance mirror into the optical cavity, where it is typically undergoes 100 reflections before it is transmitted through the second mirror and onto the detector. The present system thereby provides a higher number of reflections, and the CEAS approach results in the interrogated sample volume being greatly reduced.

In addition, the present CEAS technique facilitates potential pathlength enhancement of a factor of 100, and allows for the integration of CEAS mirrors directly onto a microfluidic device using a microfabrication approach. This approach has typical mirror separations in the micrometre and sub millimetre ranges, allowing for interrogated sample volumes which generally fall in the range of between 1 femtolitre and 25 nanolitres. Interrogated sample volumes frequently fall between 1 and 100 picolitres, for example, and such values are in the region of around 1000-fold lower than is the case with prior art documents such as U.S. Pat. No. B6,839,140, wherein the minimum interrogated sample volume is about 500 nanolitres. Indeed, the flow cell used within the prior art system of U.S. Pat. No. B6,839,140 receives the liquid sample from an external source, such as an analytical separation column attached to HPLC or CE instruments, whereas the present approach allows both CEAS detection and complex fluidic processing, such as analytical separations, to be integrated on the same microfluidic device.

SUMMARY OF THE INVENTION

Thus, according to a first aspect of the present invention, there is provided an apparatus for the detection of the spectral absorption properties of a fluid in a microenvironment, said apparatus comprising a radiation source, a microfluidic device and detection means, wherein said apparatus additionally comprises means for increasing the path length of said radiation through said fluid.

Preferred radiation sources include high powered LEDs and diode lasers. The emitted radiation may be either single wavelength or broadband. Typical detection means may, for example, be a photodiode, a 2D detector such as a charge coupled device (CCD), or a spectrograph. Said microfluidic devices may be passive devices, such as miniaturised plates which include a planar substrate which is functionalised, or micro-well plates. Alternatively, said microfluidic devices may be active devices, which are generally referred to as Lab-on-a-chip. Preferably, said fluid comprises a liquid.

The means for increasing the path length of the radiation through the fluid preferably comprises two highly reflective mirrors which cause the base path length through the fluid to be increased by many orders of magnitude. Said mirrors comprise convex or, more preferably, concave or planar mirrors. In a first embodiment of the invention, said mirrors are placed on opposing sides of said microfluidic devices and are optionally spaced apart therefrom. Alternatively, in a second embodiment, said mirrors may be integral with said microfluidic devices. In said second embodiment, said mirrors comprise mirrored surfaces which are directly coated on surfaces of said microfluidic devices, for example by direct sputtering of metal and/or dielectric layers onto the end walls of the microfluidic device, these being the walls through which a beam of radiation first enters, and then exits, the device.

When said mirrors are spaced apart from said microfluidic devices, then either concave or planar mirrors may be employed to preferably create a cavity with at least one concave element. However, when said mirrors are integral to the microfluidic devices then a convex structure, which functions as a concave mirror in the cavity, is preferred.

Radiation losses may occur, for example as a result of absorption by elements of the microfluidic device, or by scattering therefrom. However, such losses may be minimised by various means including, for example, the use of at least one slit through which the radiation is caused to pass. The slit may be located externally from the microfluidic device or may be integrated onto the outer walls of said device. Alternatively, the losses may be minimised by the use of at least one masking element which is preferably embedded as part of the microfluidic device. In an alternative embodiment, radiation losses are minimised by the use of additional mirrors, which may be deposited on the side walls of the microfluidic device.

According to a second aspect of the present invention, there is provided a method for the detection of the spectral absorption properties of a fluid in a microenvironment, said method comprising exposing a fluid contained in a microfluidic device to radiation, causing said radiation to pass through said fluid, and detecting said radiation after its passage through said fluid, wherein said method is performed in an apparatus which comprises means for increasing the path length of said radiation through said fluid.

As will be apparent to the skilled reader, said method is most suitably performed using an apparatus according to the first aspect of the invention.

The present invention thus uses the CEAS method for detection in microfluidic devices, including active and passive devices. Such microfluidic devices allow complex processing through respectively their architecture and robotic control. However, since these types of devices have low detection volumes, highly sensitive methods of detection are required. The use of CEAS, rather than CRDS, in microfluidic devices facilitates efficient, yet inexpensive, detection. The CRDS method would be significantly more expensive, since it requires a compromise between path length and fast detection; given that the path length for microfluidic devices is inherently small, expensive fast detection systems would be required.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

The present invention will now be illustrated, though without limitation, by reference to the accompanying drawings, wherein.

DESCRIPTION OF THE INVENTION

Figure 1:
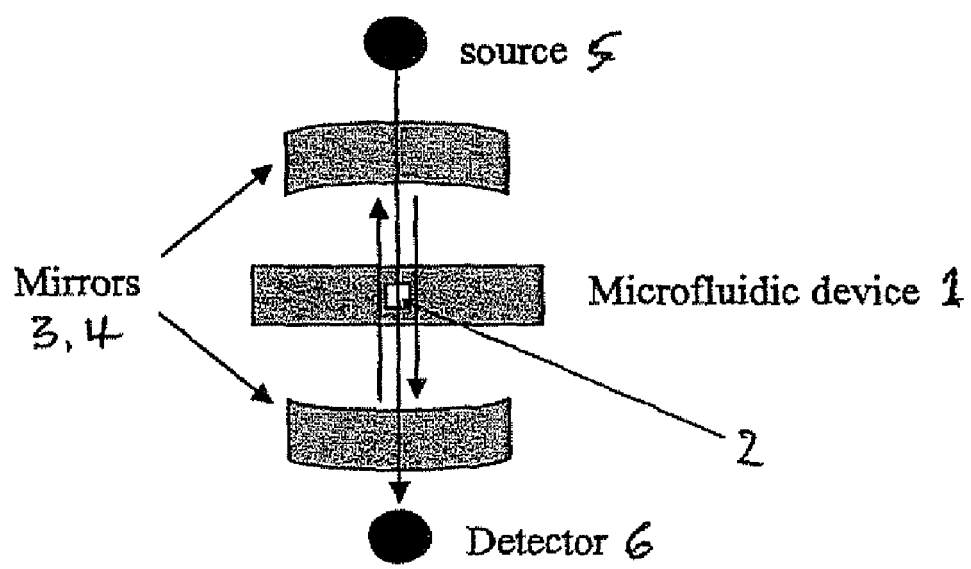
FIG. 1 shows an example of an apparatus according to a first aspect of the invention comprising a microfluidic device with a radiation source, detection means and external mirrors arranged for Cavity Enhanced Absorption Spectroscopy.

The invention provides a method and apparatus which allow for the detection of the spectral absorption properties of a fluid in a microenvironment by means of Cavity Enhanced Absorption Spectroscopy. The microenvironment may comprise a microfluidic device comprising at least one microchannel formed in a substrate through which the fluid may flow, allowing for measurements to be taken on a continuous basis; such microfluidic devices are generally referred to as a Lab-on-a-chip. Typically, the overall section of said microchannels may be anything from about 1 $\mu m^2$ to about 1 $mm^2$, thereby providing mirror separations in the micrometre and sub millimetre ranges. In certain preferred embodiments of the invention, mirror separations are generally in the range from about 10 μm to about 100 μm.

The mirror separations employed in the method and apparatus of the present invention allow for accurate measurements to be obtained by the use of sample volumes which are significantly lower than in the devices of the prior art, giving the present method and apparatus much wider applicability. Thus, interrogated sample volumes generally fall in the range of between 1 femtolitre and 25 nanolitres, with typical volumes being between, for example, 1 and 100 picolitres.

Alternatively, the microenvironment may comprise a microfluidic device, having at least one microchannel of the above dimensions, in which a discrete sample of fluid is placed, thereby permitting measurements to be made in batchwise fashion; for the purposes of the present invention, the microfluidic devices used for batchwise analysis comprise miniaturised plates, which may be planar or may contain micro-wells. The surface of miniaturised plates may optionally be functionalised in a defined pattern and such that the fluid could be deposited over the functionalised surface in either a batchwise or continuous manner. In the case of a planar functionalised plate, a microchannel formed within the substrate will be used to transport the fluid to the functionalised area. A CCD detector would be preferred for obtaining images of the patterned functionalised surface. In the context of the present invention, the term "microfluidic devices" is taken to indicate devices which may be used for continuous or batchwise purposes, except where otherwise indicated.

Microfluidic devices allow for the complex handling of small volumes of fluids for chemical and biological processing. A variety of methods may be employed for fluidic propulsion in such devices, including capillary forces, centrifugal, external pressure, electrokinetic, osmotic and acoustic methods. In the case of electrokinetic propulsion, electrodes may either be integrated onto the microfluidic device or not integrated onto the said device. Centrifugal methods, on the other hand, are normally implemented in a disk format and are particularly convenient for parallelization or paralleling of processing, whereas external pressure methods often use a syringe, which can become more difficult with long thin capillary channels which require the use of high pressures to propel the fluid. The use of acoustic pumping, however, is at an early stage and has not been realised for practical devices.

Microfluidic devices may be fabricated from a wide variety of substrates, including glass, quartz, polymers, silicon, and hybrid materials which involve a combination of materials. Several microfabrication approaches can be adopted for the creation of microfluidic devices, and the choice of which approach to adopt is dependent on a number of factors including: the substrate to be used, the function(s) to be implemented, and the volume of devices to be produced. Large volume of devices are generally created using high replication approaches such as photolithography, hot embossing, micro-injection moulding, roll replication and direct plasma etching. Microfluidic devices are also subjected to a variety of post-processing treatments, which may include laser welding, thermal bonding, ultrasonic bonding, adhesive, hole drilling and surface modification.

Serial production of devices can be achieved through, for example, micro machining, laser ablation, powder blasting, micro-stereolithography, soft lithography and nanoimprinting. In addition, microfluidic devices often require some form of metallization and this can be achieved through a variety of approaches, including sputtering. Thus, fabrication of a particular microfluidic device could require a combination of approaches, e.g. photolithography, or the use of precision milling to produce the mould for use in either hot embossing or micro-injection moulding.

Preferred embodiments of the apparatus according to the present invention include:
  (i) Apparatus wherein the microfluidic device is placed between two external high reflectivity concave mirrors in a suitable part of the electromagnetic spectrum;
  (ii) Apparatus wherein the microfluidic device includes highly reflective concave or planar mirrors incorporated on the surface thereof, in order to achieve integrated microfluidic optical cavity detection; and
  (iii) Apparatus of type (i) or type (ii) wherein the microfluidic device comprises a miniaturised plate which may comprise a planar substrate with an array of receptors, or could comprise micro-wells.

In the case of integrated microfluidic optical cavity detection, the mirrors can be fabricated through direct sputtering of a metal and/or dielectric layer(s) onto the microfluidic device. A microfabricated approach for creation of the microfluidic device and mirror will provide greater control of cavity alignment and geometry. In the apparatus according to the present invention, the liquid may be in contact with the mirrors; alternatively, the mirrors are either external to the fluidic device or are integrated on external walls of the microfluidic device. In any event, the mirrors are adapted so as to provide internal reflection within the microfluidic device.

When carrying out batchwise measurements using miniaturised plates, either single or multiple radiation sources and detectors may be employed. In addition, scanning of the individual elements of the miniaturised plates may be carried out either by control of the x-y stage on which the plates are mounted, or by manipulation of the detector system.

Of the possible detection means available for use in conjunction with the apparatus and method of the invention, 2D detection allows a 2D image of the substrate to be formed, and is preferred for optical detection for planar substrates patterned with an array of receptors, the resulting technique being known as Cavity Enhanced Imaging (CEI). Wavelength information may be obtained by inserting a liquid crystal tunable filter (LCTF) between the cavity and the 2D detector, whereupon scanning the LCTF would enable the spectral profile of the 2D image to be obtained. In an alternative embodiment, Cavity Enhanced Spectral Imaging (CESI) may be accomplished by adopting one of the following approaches:
  (a) stepping a suitable single element photodiode or linear array across the image on a motorised x-y stage with a LCTF being raster scanned to provide spectral information; or
  (b) stepping a fibre optic with suitable imaging optics, attached to a spectrograph, across the image on a motorised x-y stage to obtain a cavity enhanced spectral image.

Preferred embodiments of the invention are illustrated in the drawings to which specific reference will now be made. Dealing firstly with FIG. 1, there is shown an apparatus according to the invention which includes an embedded channel and an optical set-up comprising a focused excitation beam and two external mirrors. Thus, the apparatus comprises a microfluidic device (1) including a microchannel (2) located between highly reflective mirrors (3,4). Radiation is supplied from source (5) and passes through the fluid contained in the microchannel (2) of the microfluidic device (1), being then confined between the two mirrors (3,4), thereby resulting in the base path length being increased by many orders of magnitude. Eventually, the radiation passes to the detector (6) wherein a measurement is taken.

The microfluidic device in this embodiment may be created by a variety of high replication approaches, such as photolithography with etching, hot embossing and micro-injection moulding or, alternatively, through serial processing, such as laser ablation, precision milling or powder blasting. Such microfluidic devices are typically fabricated in two parts, the body of the device incorporating the fluidic architecture, and a lid incorporating the fluidic inlet and outlet ports. Alternatively, the fluidic architecture may include one of the fluidic inlet and outlet ports, with the other comprised in the lid, or the fluidic architecture may comprise both the fluidic inlet and outlet ports, thereby leaving the lid to seal the overall element. Bonding of the lid onto the main body of the device can be carried out by processes such as ultrasonic and thermal bonding. CEAS detection may be performed by placing the microfluidic device in an optical set-up that focuses the radiation on the channel, and wherein the two external mirrors reflect at least 80% of the radiation in order to enhance its path length, and transmit the remaining part of the radiation to the external detector.

The lid and body of the microfluidic device may absorb and scatter the radiation before and after its absorption by the compound of interest in the microfluidic channel. This is particularly important when the beam is wider than the microchannel. The radiation losses may be minimised in a number of ways, including the use of an external slit or an integrated slit on the outer walls of the device, and the use of a masking element embedded as part of the microfluidic device.

Figure 2:
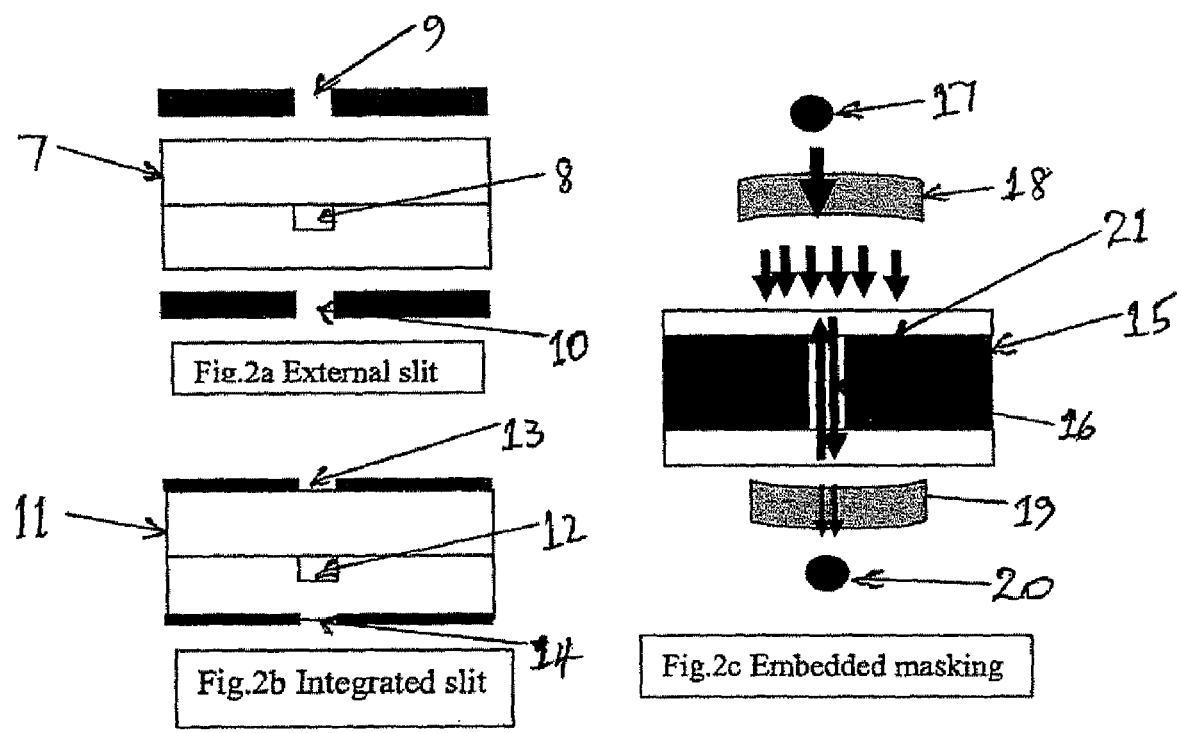
FIGS. 2(a), (b) and (c) illustrate additional examples of apparatus comprising external mirrors, further adapted to prevent absorbance and/or scattering of light by the provision of, respectively, external slits, integrated slits and embedded masking.

These features may be illustrated by reference to FIG. 2, wherein there is shown, in FIG. 2(a), a microfluidic device (7) including a microchannel (8) either side of which are placed external slits (9,10) which help to prevent the absorbance and/or scattering of light from the side wall of the channel (8). In this arrangement, however, there is a requirement for good alignment between the slits (9,10) and the microfluidic device (7).

Thus, as an alternative, there is provided an apparatus as shown in FIG. 2(b) which comprises a microfluidic device (11) including a microchannel (12) wherein integrated slits (13,14) are fabricated onto the device, thereby simplifying the alignment issues. In the said embodiment, the top and bottom walls of the microchannel (12) may absorb and scatter the light before and after the absorption of the fluid under investigation in the microfluidic device (11). Consequently, the top and bottom walls of the device should be kept as thin as possible, or coated with suitable anti-reflecting coatings, in order to limit this effect.

As a further alternative, in FIG. 2(c) there is illustrated a microfluidic element (15) incorporating a microchannel (16) through which a fluid may pass. The apparatus also comprises radiation source (17), external mirrors (18,19) and detector (20). In addition, there is provided, in the microfluidic device (15), an embedded masking element (21), adapted so as to prevent absorbance and/or scattering of light by the body of the microfluidic device (15). In the illustrated embodiment, the masking element (21) comprises a thick opaque material element, which incorporates the fluidic architecture, so as to prevent interference from absorption and scattering of light. In an alternative arrangement, the masking element (21) may, for example, comprise a metal layer, sandwiched between the lid and body of the microfluidic device (15) in order to reflect the light.

The different architectures described can all be implemented for an array of detection chambers for array based analysis.

Figure 3:
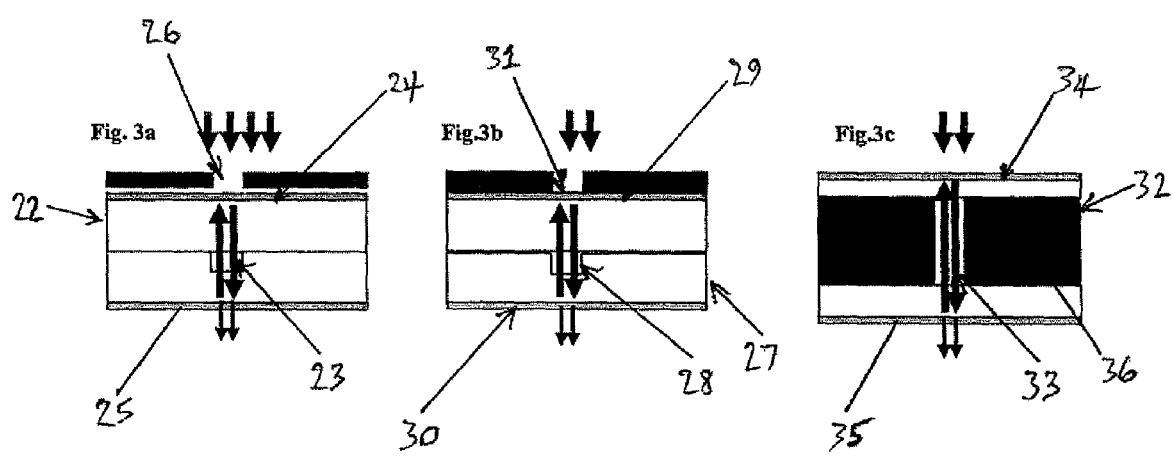
FIGS. 3(a), (b) and (c) illustrate sections of alternative apparatus according to the first aspect of the invention and show microfluidic devices comprising integral mirrors which, in the embodiments illustrated, are adapted to prevent absorbance and/or scattering of light by the provision of, respectively, external slits, integrated slits and opaque material within the fluid architecture.

Turning now to FIG. 3, there are illustrated embodiments of the invention wherein mirrors are integrated on a microfluidic device for on-chip optical cavity detection. Thus, in FIG. 3(a) there is shown a microfluidic device (22) including a microchannel (23) wherein mirrors (24,25) are deposited on the surfaces of the microfluidic device, and the apparatus is additionally provided with an external slit (26) in an analogous fashion to the apparatus of FIG. 2(a). The use of an external slit in this way facilitates the blocking-off of any contribution of the side walls in the measurements. However, good alignment between the slit and the microfluidic part is important in order to avoid any absorption and/or scattering of light from the side wall of the channel.

In FIG. 3(b) there is illustrated a microfluidic device (27) which incorporates a microchannel (28), with mirrors (29,30) deposited on the faces of the microfluidic device, the apparatus additionally being provided with an integrated slit (31), in an analogous fashion to the apparatus of FIG. 2(b). Said integrated slit (31) obviates the alignment difficulties of the apparatus of FIG. 3(a), and may be integrated on top of the mirror (29) by metal patterning.

In a further embodiment, analogous to the apparatus of FIG. 2(c), there is shown in FIG. 3(c) an apparatus comprising a microfluidic device (32) incorporating a microchannel (33) and mirrors (34,35), wherein an opaque polymer (36) with the fluidic architecture is sandwiched between the sealing plates (not shown) and the mirrors (34,35), the opaque polymer (36) being used to prevent interference due to absorbance and scattering of light.

The particular embodiment of the invention wherein the mirrors are integrated as part of the microfluidic device, is generally more convenient. A variety of thin layer deposition approaches can be used for deposition of a high reflectivity mirror, including sputtering, e-beam lithography and thermal evaporation. Generally, the most appropriate method is dependent on the substrate being used and the correct choice in this regard would be familiar to those skilled in the art.

The thin layer deposition process is required to produce a sufficiently reflective mirror having good adhesion. Preferred layers are either dielectric or metallic layers, where the reflectivity is determined by controlled deposition of appropriate materials, such as metals. Poor adhesion of the thin layer may be alleviated by surface treatment or complementary adhesion layer deposition. Since the internal surface is required to be highly reflective, the additional adhesion layer should be thin in order to avoid absorption and scattering of the light from the microfluidic element.

Figure 4:
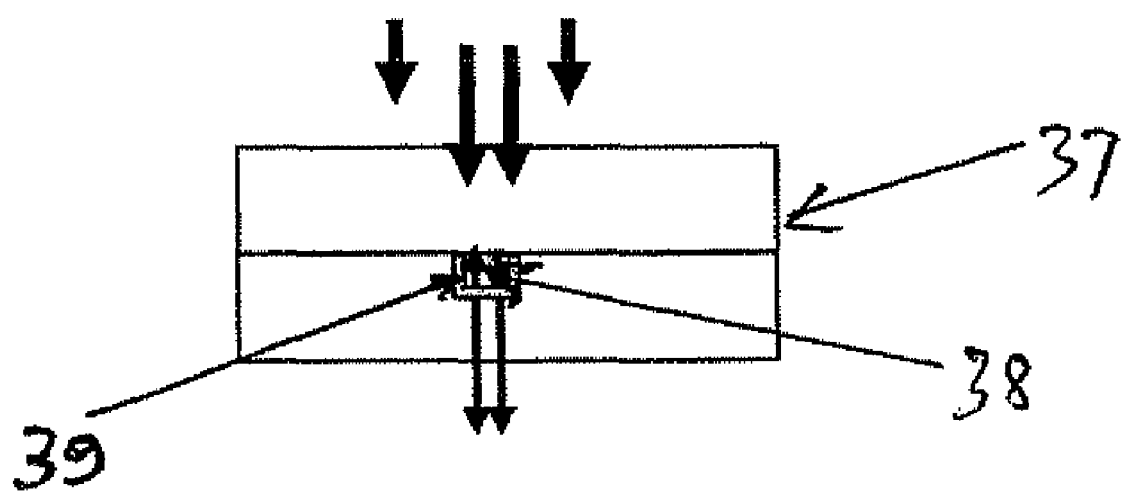
FIG. 4 shows a further example of apparatus comprising integral mirrors which, in this case, includes internal mirrors deposited on the side walls of the microchannel through which the fluid flows.

A further embodiment of the invention is shown in FIG. 4, wherein there is illustrated a microfluidic device (37) including microchannel (38) wherein mirrors (39) are integrated on the walls of the microchannel (38) at the detection area. These mirrors may be deposited at the end face of the lid and microchannel (38) before sealing. In addition, mirrors can be deposited on the side walls to prevent losses at these points, as shown in the embodiment of FIG. 4. In this embodiment the solution in the microchannel (38) comes into direct contact with the mirror and, therefore, there is a potential for fouling of the mirrors. In such cases, it is necessary that an appropriate cleaning regime is implemented.

In the apparatus of the invention, the mirrors may be integrated in either planar, concave or convex forms, but preferably are integrated in planar or concave forms. In the case of mirrors that are located on the internal walls of the microchannel, then a more stable optical cavity is formed when at least one of the mirrors has a concave form. For those embodiments wherein the mirrors are integrated onto the top and bottom of the microfluidic device, then the formation of a more stable cavity is achieved when at least one of the structures on the microfluidic device takes a convex form, thereby functioning as a concave mirror in the cavity.

Various approaches are available for producing such concave and convex mirrors, and these would be known to those skilled in the art. The particular method employed in a given situation would in part be dependent on the type of microfluidic substrate involved. A concave mirror could, for example, be formed by firstly producing a curved surface at a defined location and then subsequently using a metal/dielectric deposition technique. Planar mirrors produce less stable cavities, but are easier to fabricate and would provide appropriate performance for certain applications.

The architectures described with integrated mirrors for on-chip optical CEAS detection can be implemented for an array of detection chambers for array based sensing.

Figure 5:
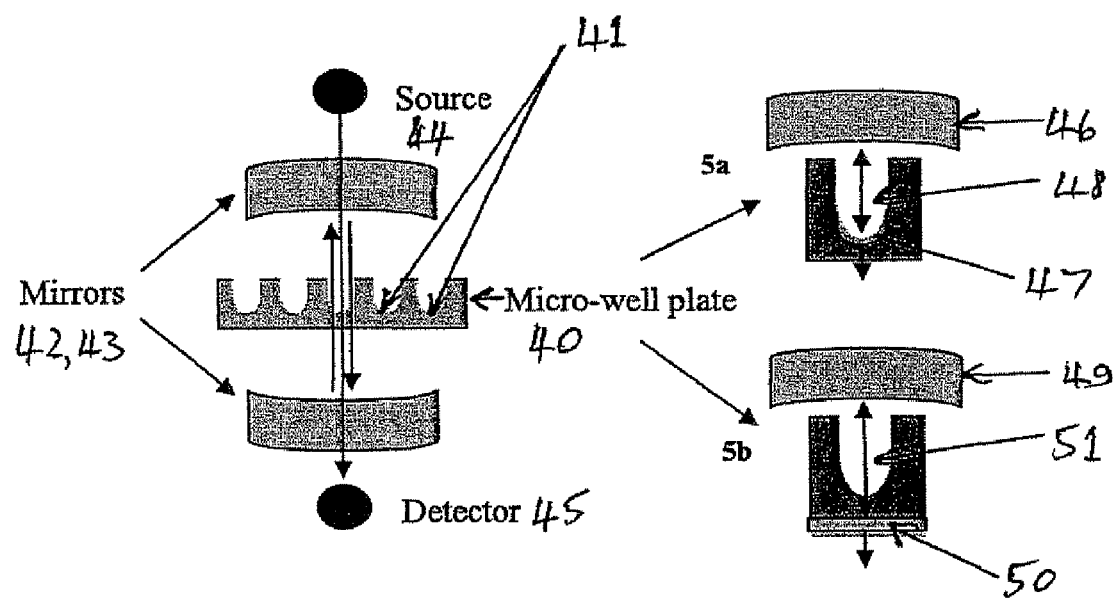
FIG. 5 shows an example of an apparatus according to the first aspect of the invention wherein the microfluidic device comprises a micro-well plate.

FIG. 5 illustrates the method and apparatus of the present invention in a situation wherein the microfluidic device comprises a micro-well plate. Thus, the first arrangement depicted in FIG. 5 shows an apparatus comprising a micro-well plate (40) which includes wells (41), with mirrors (42,43) being positioned on either side of the plate (40). Radiation is supplied by a source (44), and emerging radiation is collected by the detector (45). In this arrangement, the mirrors are implemented externally, in between the light source and the detector and, once the mirrors are aligned on the optical set-up, scanning of either the micro-well plate or the reader will provide scanning over an array of micro-well elements.

Further possible arrangements are also shown in FIG. 5. Thus, FIGS. 5(a) and 5(b) show apparatus wherein one external mirror (46,49) is used, and the second mirror is deployed either in the well plate or on the backside of the micro-well plate. In the arrangement shown in FIG. 5(a), the direct deposition of the mirror (47) inside the well (48) would reduce interference from scattering of light, whereas deposition of the mirror (50) on the backside of the well (51), as shown in FIG. 5(b) has the advantage avoiding direct contact of the mirror with the liquid sample in the well.

In the embodiments depicted in FIG. 5, the Cavity Enhanced Absorption Spectroscopy technique may employ either single or multiple light sources and detectors and an x-y stage adapted for controlled movement of the micro-well plates. Again, the light source could include a high powered LED or diode laser, and detection means may comprise a photodiode, a 2D detector such as a charge coupled device (CCD), or a spectrograph.

Figure 6:
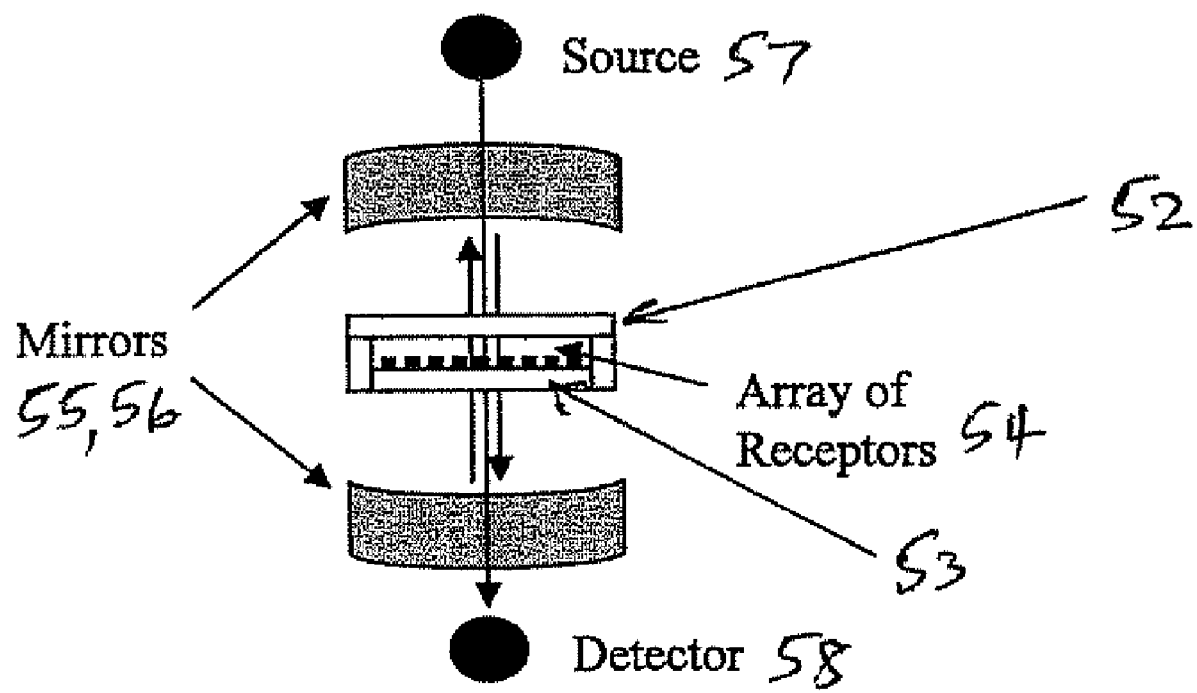
FIG. 6 shows an example of an apparatus according to the first aspect of the invention wherein the microfluidic device comprises a planar substrate.

Finally, there is shown in FIG. 6 an apparatus according to the present invention wherein the microfluidic device (52) comprises a planar substrate (53) which is functionalised with an array of bioactive components (54), with mirrors (55,56) being positioned on either side of the device (52). Radiation is supplied by a source (57), and emerging radiation is collected by the detector (58). The mirrors are implemented externally, in between the light source and the detector. Preferably, the detector (58) comprises a 2D detection system, allowing a 2D image of the substrate to be formed.

REFERENCES

1. A. O'Keefe and D. A. G. Deacon, *Rev. Sci. Instrum.* 59, p 2544 (1988).
2. R. Engeln, G. Berden, R. Peeters and G. Meijer, *Rev. Sci. Instrum.* 69, p 3763 (1998).
3. A. O'Keefe, *Chem. Phys. Lett.,* 293, p 331 (1998).
4. S. E. Fiedler, A. Hese and A. A. Ruth, *Chem. Phys. Lett.,* 371, p 284 (2003).
5. S. M. Ball, J. M. Langridge and R. L. Jones, *Chem. Phys. Lett.,* 398, p 68-74 (2004).
6. K. L. Snyder and R. N. Zare. Cavity Ring-Down Spectroscopy as a Detector for Liquid Chromatography, *Anal. Chem.,* 75 (13), 3086-3091, 2003.
7. A. J. Hallock, E. S. F. Berman, and R. N. Zare Direct Monitoring of Absorption in Solution by Cavity Ring-Down Spectroscopy *Anal. Chem.,* 74 (7), 1741-1743, 2002.
8. A. J. Hallock, E. S. F. Berman and R. N. Zare, Use of Broadband, Continuous-Wave Diode Lasers in Cavity Ring-Down Spectroscopy for Liquid Samples, Applied Spectroscopy, Volume 57, Number 5, May 2003, pp. 571-573(3).
9. B. Bahnev, L. van der Sneppen, A. E. Wiskerke, F. Ariese, C. Gooijer, and W. Ubachs, Miniaturized Cavity Ring-Down Detection in a Liquid Flow Cell, *Anal. Chem.,* 77 (4), 1188-1191, 2005.

The invention claimed is:

1. An apparatus for detection of spectral absorption properties of a fluid in a microenvironment, said apparatus comprising:
   a radiation source;
   a detection means including detection by Cavity Enhanced Absorption Spectrometry;
   a microfluidic device positioned between said radiation source and said detection means; and
   means for increasing a path length of radiation through said fluid,
   wherein an interrogated sample volume of said fluid flows through said microfluidic device and is between 1 femtoliter and 25 nanoliters.

2. The apparatus of claim 1, wherein said detection means comprises detection by Cavity Enhanced Imaging (CEI) or Cavity Enhanced Spectral Imaging (CESI).

3. The apparatus of claim 1, wherein the radiation source emits either single wavelength or broadband radiation, and comprises a high powered LED or diode laser, and wherein the detection means comprises a photodiode, a spectrograph, or a 2D detector such as a charge coupled device (CCD).

4. The apparatus of claim 1,
   wherein the microfluidic device facilitates storage, dosing, movement and mixing of very small volumes of fluids and includes passive or active components, and
   wherein said passive components comprise plates that are functionalised and said active components perform integrated functions including sample preparation, separation and detection.

5. The apparatus of claim 1, wherein the apparatus comprises at least one microchannel, and wherein an overall section of said at least one microchannel is about 1 $\mu m^2$ to about 1 $mm^2$.

6. The apparatus of claim 1, wherein the apparatus is configured to handle small volumes of fluids for chemical and biological processing.

7. The apparatus of claim 1, wherein the means for increasing the path length of the radiation comprises two reflective mirrors which increase the base path length through the fluid by many orders of magnitude.

8. The apparatus of claim 7, wherein the mirrors comprise convex, concave or planar mirrors, and wherein said mirrors are either spaced apart from said microfluidic device, or are integral with said microfluidic device.

9. The apparatus of claim 8, wherein said mirrors are integral with said microfluidic device and comprise mirrored surfaces which are directly coated on said microfluidic devices.

10. The apparatus of claim 9, wherein said mirrors are coated on said microfluidic devices by e-beam lithography, thermal evaporation or direct sputtering of metal or dielectric layers onto the end walls of the microfluidic devices.

11. The apparatus of claim 1, wherein the apparatus additionally comprises at least one slit through which the radiation passes, and wherein said slit is located externally from the microfluidic device or is integrated onto outer walls of the microfluidic device.

12. The apparatus of claim 1, further comprising additional mirrors to minimize radiation losses.

13. The apparatus of claim 1, wherein the microfluidic device is fabricated from at least one of glass, quartz, silicon, polymeric materials, or hybrid materials thereof.

14. The apparatus of claim 1, wherein the microfluidic device is fabricated by at least one microfabrication approach selected from photolithography, hot embossing, laser ablation, micro-injection moulding, roll replication, direct plasma etching, micro machining, powder blasting, microstereolithography, soft lithography and nanoimprinting.

15. The apparatus of claim 1, wherein fluidic propulsion of the microfluidic device is achieved by capillary forces, centrifugal, external pressure, electrokinetic, osmotic or acoustic methods.

16. A method for detection of the spectral absorption properties of a fluid in a microenvironment, said method comprising:

exposing a fluid contained in a microfluidic device to radiation;

causing said radiation to pass through said fluid; and detecting said radiation after passage thereof through said fluid, wherein said method is performed using the apparatus of claim 1.

* * * * *